US008748425B2

(12) United States Patent
Chang et al.

(10) Patent No.: US 8,748,425 B2
(45) Date of Patent: *Jun. 10, 2014

(54) COMBINATION OF BRIMONIDINE AND TIMOLOL FOR TOPICAL OPHTHALMIC USE

(71) Applicant: Allergan Sales, LLC, Irvine, CA (US)

(72) Inventors: Chin-Ming Chang, Tustin, CA (US); Gary J. Beck, Fullerton, CA (US); Cynthia C. Pratt, Mission Viejo, CA (US); Amy L. Batoosingh, Mission Viejo, CA (US)

(73) Assignee: Allergan Sales, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/957,287

(22) Filed: Aug. 1, 2013

(65) Prior Publication Data
US 2013/0324534 A1    Dec. 5, 2013

Related U.S. Application Data

(63) Continuation of application No. 13/801,252, filed on Mar. 13, 2013, which is a continuation of application No. 13/727,106, filed on Dec. 26, 2012, which is a continuation of application No. 13/308,507, filed on Nov. 30, 2011, now Pat. No. 8,354,409, which is a continuation of application No. 11/946,828, filed on Nov. 28, 2007, now Pat. No. 8,133,890, which is a continuation of application No. 10/685,941, filed on Oct. 14, 2003, now Pat. No. 7,320,976, which is a continuation of application No. 10/126,790, filed on Apr. 19, 2002, now Pat. No. 7,030,149.

(51) Int. Cl.
*A61K 31/5377* (2006.01)
*A61K 31/498* (2006.01)
*A61K 31/4168* (2006.01)

(52) U.S. Cl.
CPC ........... *A61K 31/5377* (2013.01); *A61K 31/498* (2013.01); *A61K 31/4168* (2013.01)
USPC ......... 514/236.2; 514/248; 514/397; 514/398

(58) Field of Classification Search
CPC ............ A61K 31/5377; A61K 31/498; A61K 31/4168
USPC .............................. 514/236.2, 249, 397, 398
See application file for complete search history.

(56) References Cited

U.S. PATENT DOCUMENTS

| | | |
|---|---|---|
| 3,890,319 A | 6/1975 | Danielewicz |
| 4,029,792 A | 6/1977 | Danielewicz |
| 4,195,085 A | 3/1980 | Stone |
| 4,861,760 A | 8/1989 | Mazuel |
| 4,910,225 A | 3/1990 | Ogawa |
| 5,021,410 A | 6/1991 | Burke |
| 5,215,991 A | 6/1993 | Burke |
| 5,290,781 A | 3/1994 | Espino |
| 5,502,052 A | 3/1996 | DeSantis |
| 5,564,596 A | 10/1996 | Meadows |
| 5,795,913 A | 8/1998 | Lehmussaari |
| 5,827,862 A | 10/1998 | Yamamura |
| 5,856,329 A | 1/1999 | Wheeler |
| 5,883,108 A | 3/1999 | DeSantis |
| 6,146,622 A | 11/2000 | Castillo |
| 6,159,458 A | 12/2000 | Bowman |
| 6,174,524 B1 | 1/2001 | Bawa |
| 6,194,415 B1 | 2/2001 | Wheeler |
| 6,242,442 B1 | 6/2001 | Dean |
| 6,248,741 B1 | 6/2001 | Wheeler |
| 6,294,563 B1 | 9/2001 | Garst |
| 6,316,441 B1 | 11/2001 | Dean |
| 6,410,045 B1 | 6/2002 | Schultz |
| 6,440,964 B1 | 8/2002 | Cagle |
| 6,441,047 B2 | 8/2002 | DeSantis |
| 6,562,873 B2 | 5/2003 | Olejnik |
| 6,627,210 B2 | 9/2003 | Olejnik |
| 6,740,664 B2 | 5/2004 | Cagle |
| 7,030,149 B2 | 4/2006 | Chang |
| 7,320,976 B2 | 1/2008 | Chang |
| 7,323,463 B2 | 1/2008 | Chang |
| 7,642,258 B2 | 1/2010 | Chang |
| 2002/0071874 A1 | 6/2002 | Olejnik |
| 2002/0128267 A1 | 9/2002 | Bandyopadhyay |

FOREIGN PATENT DOCUMENTS

| | | |
|---|---|---|
| CA | 2225626 | 1/1997 |
| CA | 2440764 | 10/2003 |
| EP | 0426390 | 8/1991 |
| EP | 1496912 | 10/2003 |
| WO | 95-16449 | 6/1995 |
| WO | 03-088973 | 10/2003 |

OTHER PUBLICATIONS

"United States District Court for the Eastern District of Texas Marshall Division, Allergan's Proposed Post-Trial Findings of Fact and Conclusions of Law"; *Allergan v. Sandoz*; Aug. 10, 2011.
"United States District Court for the Eastern District of Texas Marshall Division, Defendant's Post—Trial Proposed Findings of Fact and Conclusions of Law"; *Allergan v. Sandoz*; Aug. 10, 2011.
"United States District Court for the Eastern District of Texas Marshall Division, Finding of Facts and Conclusions of Law" *Allergan v. Sandoz*; Aug. 22, 2011.

(Continued)

*Primary Examiner* — Bong-Sook Baek
(74) *Attorney, Agent, or Firm* — Lorenz Siddiqi

(57) ABSTRACT

Disclosed are pharmaceutical compositions comprising brimondine and timolol for topical ophthalmic delivery and a method of treatment comprising administering said composition when indicated for glaucoma and associated conditions such as elevated intraocular pressure in the eyes of humans.

8 Claims, No Drawings

(56) References Cited

OTHER PUBLICATIONS

Adkins, Julie, Brimonidine—a review of its pharmacological properties and clinical potential in the management of open-angle glaucoma and ocular hypertension, Drugs Aging, 1998, 225-241, 12.
Airaksinen, Juhani et al, A Double Masked Study of Timolol and Pilocarpine Combined, American Journal of Ophthalmology, Dec. 15, 1987, 587-590, 104.
*Allergan, Inc. v. Sandoz In., Alcon Laboratories, Inc., Alcon Research, Ltd., Alcon, Inc., and Falcon Pharmaceuticals, Ltd., and Apotex Inc. And Apotex Corp., and Watson Laboratories, Inc.*, (Fed. Cir. 2013) 20 Pages.
Apotex, Inc.; "Letter Regarding Apotex's Proposed Brimonidine/Timolol Ophthalmic Product Paragraph IV Certification-U.S. Patent Nos. 7,030, 149, 7,323,463, 7,320,976, and 7,642,258"; May 12, 2010.
Arici, MK et al, A Short Term Study of the Additive Effect of Timolol and Brimonidine on Intraocular Pressure, Eye 2002, Jan. 1, 2002, 39-43, 16 (1), Nature Publishing Group.
Arvo, 1999 Annual Meeting Fort Lauderdale, Florida May 9-May 14, Association for Research in Vision and Ophthalmology, Mar. 15, 1999, 4, 40(4), US.
Arvo, 2001 Annual Meeting Fort Lauderdale, Florida Apr. 29-May 4, Investigative Ophthalmology & Visual Science, Mar. 15, 2001, S822, 2 pgs, 42(4), The Association for Research in Vision and Ophthalmology, US.
Ashton, Paul et al, Formulation Influence on Conjunctival Penetration of Four Beta Blockers in the Pigmented Rabbit: A Comparison with Corneal Penetration, Pharmaceutical Research, 1991, 1166-1174, 8 (9).
Barnebey, Howard et al, The Efficacy of Brimonidine in Decreasing Elevations in Intraocular Pressure after Laser Trabeculoplasty, Ophthalmology, 1993, 1083-1088, 100 (7).
Baudouin, Christophe, Side Effects of Antiglaucomatous Drugs on the Ocular Surface, Cur Op Ophth, 1996, 80-86, 7 (2).
Betoptic® Pilo Ophthalmic Suspension Product Information, Alcon Labs., Inc., 1997.
Bhatt, R. et al, Prospective Survey of Adverse Reactions to Topical Antiglaucoma Medications in a Hospital Population, Eye, 2005, 392-395, 19.
BNF, Local Anaesthetics, British National Formulary, Mar. 2002, p. 514, 3 scanned pgs, 43, British Medical Association.
Bressler, Neil et al, Age-Related Macular Degeneration, Surv. Ophthalmol., 1988, 375-413, 32 (6).
Bressler, Susan et al, Age-related Macular Degeneration: Drusen and Geographic Atrophy, Principles and Practice of Ophthalmology, 1994, 826-833, 2.
Burke, J.A. et al, Ocular Effects of a Relatively Selective α-2 Agonist {UK-14, 304-18) In Cats, Rabbits, and Monkeys, Current Eye Research, 1986, 665-676, 5(9).
Cantor, L.B. et al, Comparison of the Effect of Alphagan 0.2% versus Trusopt 2.0% in Combination with Beta-Blockers, Investigative Ophthalmology & Visual Science, Mar. 1998, S480, 39(4).
Cantor, Louis et al, Brimonidine, Exp. Opin. Invest. Drugs., 1997, 1063-1083, 6(8).
Center for Drug Evaluation and Research, Application No. 21-398, Summary Review, 2007.
Center for Drug Evaluation and Research, Application No. 21,398, Statistical Reviews, 2007.
Center for Drug Evaluation and Research, Application No. 21-398, Approvable Letter, 2006.
Center for Drug Evaluation and Research, Application No. 21-398, Medical Reviews, 2007.
Centofanti, M. et al, Comparative Acute Effects of 0.2% Brimonidine versus 2% Dorzolamide Combined to Beta-Blockers in Ocular Hypertension, Investigative Ophthalmology & Visual Science, Mar. 1998, S480, 39(4).
Choudhri, Saira et al, A Comparison of Dorzolamide-Timolol Combination Versus the Concomitant Drugs, American Journal of Ophthalmology, Dec. 2000, 833, 130(6).
Cioffi, George et al, Microvasculature of the Anterior Optic Nerve, Surv. Ophthalmol., May 1994, S107-S117, 38.
Clineschmidt, Coleen et al, A Randomized Trial in Patients Inadequately Controlled with Timolol Alone Comparing the Dorzolamide-Timolol Combination to Monotherapy with Timolol or Dorzolamide, American Journal of Ophthalmology, Oct. 1998, 1952-1959, 96(11).
Coakes, Roger et al, The Mechanism of Timolol in Lowering Intraocular Pressure in the Normal Eye, Arch. Opthalmol., Nov. 1978, 2045-2048, 96(11).
Combigan Product Label, Allergan, Inc., 11 pages, 2008.
Defendant Watson Laboratories, Inc.'SP.R. 3-3 Invalidity Contentions, Mar. 21,2011.
Craven, E.R., Efficacy and Safety of the IOP-Lowering Fixed Combination Brimonidine 0.2%/Timolol 0.5%, M200510403E.1.doc, 2005, One page.
David, Robert et al, Brimonidine in the Prevention of Intraocular Pressure Elevation Following Argon Laser Trabeculoplast, Arch. Opthalmol., Oct. 1993, 1387-1390, 111(10).
Debbasch, Caroline et al, Evaluation of the Toxicity of Benzalkonium chloride on the Ocular Surface, J. Tox. Cut. & Ocul. Tox., 2000, 105-115, 19 (2&3).
Declaration of an Expert (Rhett Schiffman) Regarding Facts Relevant to Patentability (37 C.F.R. § 1.132), U.S. Appl. No. 10/126,790, dated Jul. 27, 2004, signed Jul. 2, 2004, US Pat. No. 7,030,149 Prosecution History.
Declaration of Prior Invention in the United States or in A NAFTA or WTO Member Company to Overcome Cited Patent or Publication (37 C.F.R. § 1.131), U.S. Appl. No. 10/126,790, dated Jul. 27, 2004, US Pat. No. 7,030,149 Prosecution History.
Derick, Robert et al, Brimonidine Tartrate: A One-month Dose Response Study, Ophthalmology, 1997, 131, 104 (1).
Desai, Suketu, Ocular Drug Formulation and Delivery, Encyclopedia of Pharmaceutical Technology, 1995, 43-75, 11.
Diestelhorst, Michael et al, Comparison of Two Fixed Combinations of Latanoprost and Timolol in Open-Angle Glaucoma, Graege's Arch Clin Exp Ophthalmol, 1998, 577-581, 236.
Doyle, Williams et al, New Aqueous Inflow Inhibitors, Seminars in Ophthalmology, 1999, 159-163, 14(3).
Elman, Michael, Age-related macular degeneration, Int. Ophthalmol. Clin., 1986, 117-144, 26(2).
Fechtner, Realini et al, Fixed combinations of topical glaucoma medications, Curr. Opin. Ophthalmol., 2004, 132-135, 15(2).
Feldman, Edward, Laser Treatment of Subretinal Neovascularization, Int. Ophthamol. Clin., 1986, 15-174, 26(2).
Frishman, William et al, Cardiovascular Considerations in Using Topical, Oral, and Intravenous Drugs for the Treatment of Glaucoma and Ocular Hypertension—Focus on β-Adrenergic Blockade, Heart Disease: A Journal of Cardiovascular Medicine, 2001, 386-397, 3(6).
Gabelt, B'Ann et al, Apraclonidine and Brimonidine Effects on Anterior Ocular and Cardiovascular Physiology in Normal and Sympathectomized Monkeys, Exp. Eye. Res., 1994, 633-644, 59.
Goni, Francisco et al, Comparison of Fixed-Combination Brimonidine and Timolol with Concomitant Use of the Individual Components in Glaucoma and Ocular Hypertension: Achievement of Clinically Relevant IOP Reductions, 5th International Glaucoma Symposium (IGS), Mar. 2005, 3 pages.
Goni, Francisco, 12-week study comparing the fixed combination of brimonidine and Timolol with concomitant use of the individual components in patients with glaucoma and ocular hypertension, European Journal of Ophthalmology, 2005, 581-590, 15(5).
Gurwitz, Jerry et al, Treatment for Glaucoma: Adherence by the Elderly, Am. J. Public Health, 1993, 711-716, 83(5).
Guttman, Cheryl et al, Study Dispels Myths on Costs of Glaucoma Therapy, Managed Healthcare, Jul. 2000, 37-38.
Hecht, Gerald, Ophthalmic Preparations, Remington: The Science and Practice of Pharmacy, 2000, 819-835, 20 edition.
Hi-Tech Pharmacal, "Letter regarding abbreviated new drug application," Apr. 22, 2009.
Hi-Tech Pharmacal; "Letter Regarding Abbreviated New Drug Application Containing Paragraph IV Certification to U.S. Patent No. 7,323,463"; Nov. 11, 2009.

(56) References Cited

OTHER PUBLICATIONS

Hi-Tech Pharmacal; "Letter Regarding Abbreviated New Drug Application Containing Paragraph IV Certification to U.S. Patent No. 7,642,258"; Jan. 21, 2010.
Hodges, Norman, Preservative Testing, 13 Encyclopedia of Pharmaceutical Technology, 1996, 21-37, 13.
Hommer, A.B. et al, Efficacy and Safety of Unoprostone, Dorzolamide, and Brimonidine and Adjunctive Therapy to Timolol in Patients with primary open-angle glaucoma and ocular hypertension, Investigative Ophthalmology & Visual Science, Mar. 15, 2001, S554, 42(4).
Hoyng et al, Pharmacological Therapy for Glaucoma, Drugs 2000, 2000, 411-434, 59 (3), US.
Information on Alphagan® in the Physician's Desk Reference, 54th Ed. (2000).
Information on Alphagan® in the Physician's Desk Reference, 55th Ed. (2001).
Information on Alphagan® in the Physician's Desk Reference, 56th Ed. (2002).
Information on Cosopt® in the Physician's Desk Reference, 53rd Ed. (1999).
Information on Cosopt® in the Physician's Desk Reference, 55th Ed. (2001).
Information on Cosopt® in the Physician's Desk Reference, 56th Ed. (2002).
Information on Timoptic® in the Physician's Desk Reference, 54th Ed. (2000).
Information on Timoptic® in the Physician's Desk Reference, 55th Ed. (2001).
Information on Timoptic® in the Physician's Desk Reference, 56th Ed. (2002).
Interview Summary, Date of Interview Aug. 9, 2005, U.S. Appl. No. 10/126,790, US Pat. No. 7,030,149 Prosecution History.
Ischemia, Dorland's Illustrated Medical Dictionary, 1988, 857, 27 ed, W.B. Sunders Company.
Jackson, A.L. et al, Cardiovascular effects of Timolol, Brimonidine and Brimonidine/Timolol in combination, Investigative Ophthalmology & Visual Science, 2001, S418, 42(4).
Katz, Jay et al, Brimonidine Tartrate 0.2% Twice Daily vs Timolol 0.5% Twice Daily: 1-Year Results in Glaucoma Patients, Am. J. Ophth., 1999, 20-26, 127(1).
Konstas, Anastasios et al, Brimonidine 0.2% Given Two or Three Times Daily Versus Timolol Maleate 05% in Primary Open Angle Glaucoma, Am. J. Ophthalmology, Jun. 2001, 729-733, 131(6).
Kuwayama, Y., Sympathetic Nerve α2 Stimulants, Drug Therapy of Glaucoma, 2001, 234-236, Department of Ophthalmology, Osaka Hospital of Welfare Pension.
L'Esperance, Francis, Department of Ophthalmology, 1989, 989-991, 3rd ed.
Larsson, Lil-Inger, Aqueous Humor flow in Normal Human Eyes Treated With Brimonidine and Timolol, Alone and in Combination, Archives of Opthalmology, 2001, 492-495, 119, US.
Larsson, Lil-Inger, The Effect on Diurnal Intraocular Pressure of the Fixed Combination of Latanoprost 0.005% and Timolol 0.5% in Patients With Ocular Hypertension, Acta Ophthalmol. Scand., 2001, 125-128, 79.
Leblanc, Raymond, Twelve-Month Results of an Ongoing Randomized Trial Comparing Brimonidine Tartrate 0.2 % and Timolol 0.5 % with Glaucoma or Ocular Hypertension, Ophthalmology, Oct. 1998, 1960-1967, 105(10).
Lee, David A. et al, Emerging Perspectives on Glaucoma: highlights of a roundtable discussion, American Journal of Ophthalmology, Oct. 1, 2000, at p. S8, S1-11.
Li, Zong-Yi et al, Apoptosis in Retinitis Pigmentosa, Degenerative Disease of the Retina, 1995, 1-8.
MaClure, G.M. et al, Effect on the 24-Hour Diurnal Curve of Intraocular Pressure on a Fixed Ration Combination of Timolol 0.5% and Pilocarpine 2% in Patients With COAG Not Controlled on Timolol 0.5%, British Journal of Ophthalmology, 1989, 827-831, 73.
Maus, Todd et al, Comparison of the Early Effects of Brimonidine and Apraclonidine as Topical Ocular Hypotensive Agents, Arch. Ophthalmol., 1999, 586, 117.
McKinnon, S.J., Glaucoma, apoptosis, and neuroprotection, Curr. Opin. Ophthalmol., Apr. 1997, 28-37, 8(2).
Melamed, Sholomo et al, Ongoing Clinical Assessment of the Safety Profile and Efficacy of Brimonidine Compared with Timolol: Year-Three Results, Clin. Ther., 2000, 103-110, 22(1).
Merck & Co., Inc. "Cosopt® (dorzolamide hydrochloride-timolol maleate ophthalmic solution) data sheet"; NDA 20-869/S-034; Jul. 2008.
Merck & Co., Inc. "TRUSOPT® (Dorzolamide Hydrochloride Ophthalmic Solution) data sheet," NDA 20-408/S-033; Jul. 1997.
Meszaros, Elizabeth, New Pharmacotherapy Approaches Improve Focus of Glaucoma Treatment, Managed Healthcare, Jan. 1998, 44-46.
Muchnick, Bruce et al, The Optic Nerve in Glaucoma, The Optic Nerve in Clinical Practice, 1997, 103-115.
Nagasubramanian, S., A Comparison of the Ocular Hypotensive Efficacy, Safety and Acceptability of Brimonidine 0.2% Twice Daily versus Pilocarpine 2.0% Thrice Daily as Adjunct Therapy wit Beta-Blockers, Glaucoma Update IV, 2000, 203-208.
Neufeld, Arthur, New Conceptual Approaches for Pharmacological Neuroprotection in Glaucomatous Neuronal Degeneration, J. Glaucoma, Dec. 1996, 434-438, 7(6).
Nordlund, J.R. et al, Cardiovascular, Pulmonary and Ocular Hypotensive Effects of 0.2% Brimonidine, Arch. Opthalmol., Jan. 1995, 77-83, 113.
Notice of Allowability, U.S. Appl. No. 10/126,790, mail date Oct. 28, 2005, U.S. Pat. No. 7,030,149 Prosecution History.
Package Insert for Alphagen, Allergan, Inc., Dec. 20, 2001.
Package Insert for Timoptic, Merck & Co., Apr. 2000.
Package Insert for Timoptic, Merck & Co., Apr. 2001.
Package Insert for Timoptic, Merck & Co., Sep. 2005.
Patient Information brochure, "Brimonidine," www.ausdi.com, 2000.
Pharmacia Launches Dual Glaucoma Therapy, Manufacturing Chemist, Nov. 2001, 6, 72(11).
Physicians Desk Reference, Information on Alphagan® in the Physician's Desk Reference, 52nd Ed., Physicians Desk Reference 52 Edition 1998, Jan. 1, 1998, 3 Pages, 52 edition, 1998, Medical Economics Company, US.
Prescribing information for TIMOPTIC in the Physician's Desk Reference,("TIMOPTIC PDR"), Physicians' Desk Reference 52 Edition, Jan. 1, 1998, 6 Pages.
Quigley, Harry et al, Retinal Ganglion Cell Death in Experimental Glaucoma and After Axotomy Occurs by Apoptosis, Invest. Ophth. Vis. Sci., 1995, 774-786, 36.
Reply under 37 CFR § 1.111, U.S. Appl. No. 10/126,790, dated Jan. 29, 2003, US Pat. No. 7,030,149 Prosecution History. '149, p. 8.
Reply under 37 CFR § 1.111, U.S. Appl. No. 10/126,790, dated Aug. 24, 2005, US Pat. No. 7,030,149 Prosecution History. '149, pp. 2-4.
Reply under 37 CFR § 1.111, U.S. Appl. No. 10/357,622, dated Nov. 14, 2005, US Pat. No. 7,323,463 Prosecution History, pp. 3-4.
Reply under 37 CFR § 1.111, U.S. Appl. No. 10/685,941, dated Feb. 27, 2006, US Pat. No. 7,320,976 Prosecution History, p. 3-4.
Reply Under 37 CFR § 1.116 to Final Rejection, U.S. Appl. No. 10/126,790, dated May 21, 2003, US Pat. No. 7,030, 149 Prosecution History, pp. 2-3.
Reply, U.S. Appl. No. 10/126,790, dated Jul. 27, 2004, US Pat. No. 7,030,149 Prosecution History, p. 4.
Rosenthal, A.L. et al, A Comparison of the Safety and Efficacy of Brimonidine 0.2% BID Versus TID, in Subjects with Elevated Intraocular Pressure, Invest. Ophth. Vis. Sci., 1996, S1102, 37(3).
Sall, K.N. et al, A Comparison of the Ocular Hypotensive Effect of Dorzolaminde Hydrochloride/Timolol Maleate to that of the Concomitant Therapy with Brimonidine Tartate and Timolol Maleate in Patients with Ocular Hypertension or Primary open-Angle Glaucoma, Investigative Ophthalmology & Visual Science, 2001, S822, 4412-B431, 42(4).

(56) References Cited

OTHER PUBLICATIONS

Sall, Kenneth et al, Dorzolamide/Timolol Combination Versus Concomitant Administration of Brimonidine and Timolol—Six-Month Comparison of Efficacy and Tolerability, Ophthalmology, 2003, 615-624, 110.
Sandoz Canada Inc., "Letter Regarding Notice of Allegation for Brimonidine Tartrate/Timolol"; Dec. 21, 2009.
Sandoz Canada Inc., "Letter Regarding Notice of Allegation for Brimonidine Tartrate/Timolol"; Feb. 16, 2010.
Schuman, Joel et al, A 1-Year Study of Brimonidine Twice Daily in Glaucoma and Ocular Hypertension, Arch. Ophthalmol., 1997, 847-852, 115.
Schuman, Joel, Clinical Experience with Brimonidine 0.2% and Timolol 0.5% in Glaucoma and Ocular Hypertension, Survey of Opthalmology, Nov. 1996, S27-S37, 41, US.
Schuman, Joel, Effects of Systemic β-blocker Therapy on the Efficacy and Safety of Topical Brimonidine and Timolol, Ophthalmology, 2000, 1171-1177, 107(6).
Schumer, Robert A. et al, The Nerve of Glaucoma!, Archives of Opthalmology, Jan. 1994, 37-44, 112, US.
Schwartz, Bernand, Circulatory Defects of the Optic Disk and Retina in Ocular Hypertension and High Pressure Open-Angle Glaucoma, Surv. Ophthalmol., 1994, S23-S34, 38.
Serle, Janet B., Pharmacological Advances in the Treatment of Glaucoma, Drugs & Aging, 1994, 156-170, 5 (3), US.
Serle, Janet, A Comparison of the Safety and Efficacy of Twice Daily Brimonidine 0.2% Versus Betaxolol 0.25% in Subjects with Elevated Intraocular Pressure, Surv. Ophth., 1996, S39-S47, 41 (Suppl. 1).
Simmons, Steven et al, Comparison of Brimonidine with Latanoprost in the Adjunctive Treatment of Glaucoma, Clin. Ther., 2000, 388-399, 22(4).
Simmons, Steven et al, Three-month Comparison of Brimonidine and Latanoprost as Adjunctive Therapy in Glaucoma and Ocular Hypertension Patients Uncontrolled on β-blockers: Tolerance and Peak Intraocular Pressure Lowering, Ophthalmology, 2002, 307-314, 109(2).
Simmons, Steven, Efficacy of Brimonidine 0.2% and Dorzolamide 0.2% as Adjunctive Therapy to Beta-Blockers in Adult Patients with Glaucoma or Ocular Hypertension, Clin. Therapeutics, 2001, 604-619, 23(4).
Soderstrom, M.B. et al, Timolol-Pilocarpine Combined vs. Timolol and Pilocarpine Given Separately, Am. J. Ophthalmology, 1989, 465-470, 107.
Spaeth, George et al, The effects of brimonidine tartrate on the incidence of intraocular pressure (IOP) spikes following argon laser trabeculoplasty, Investigative Ophthalmology & Visual Science, 1992, 1159, 33(4).
Stewart, W.C. et al, Comparison of the Efficacy and Safety of Latanoprost 0.0005% Compared to Brimonidine 0.2% or Dorzolamide 2% When Added to a Topical β-Adrenergic Blocker in Patients with Primary Open-Angle Glaucoma or Ocular Hypertension, J. Ocu. Pharmacology and Therapeutics., 2000, 251-260, 16(3).
Stewart, William C., Perspectives in the Medical Treatment of Glaucoma, Current Opinion in Opthalmology, Apr. 1999, 99-108, 10 (2), US.
Stewart, William et al, Cardiovascular Effects of Timolol Maleate, Brimonidine or Brimonidine/Timolol Maleate in Concomitant Therapy, Acta Ophthalmol Scand., Jun. 2002, 277-281, 80(3).
Strohmaier, Kim et al, The Efficacy and Safety of the Dorzolamide-Timolol Combination Versus the Concomitant Administration of its Components, American Journal of Ophthalmology, Oct. 1998, 1936-1944, 105.
Sverrisson, T. et al, The Dorzolamide/Timolol Combination Versus Timolol Plus Pilocarpine: Patient Preference and Impact on Daily Life, J. Glaucoma, Oct. 1999, 315-324, 8(5).
Timmermans et al, Structure-Activity Relationships in Clonidine-Like Imidazolidines and Related Compounds, Progress in Pharmacology, 1980, 21-41, 3(1).
Toris, C.B. et al, Effects of Brimonidine on Aqueous Humor Dynamics in Human Eyes, Arch Ophthalmol., Dec. 1995, 1514-1517, 113.

Toyoda, K., Drugs for Use in Ophthalmology, Journal of Medicinal Drugs, 2002, 324-328(Translated), 38.
Traverso, C.E. et al, Additivity of Brimonidine 0.2% BID or Pilocarpine 2.0% TID to Beta-Blocker Monotherapy, ARVO Annual Meeting Fort Lauderdale, Florida, Invest. Ophth. Vis. Sci., Mar. 1998, S480, 39(4).
Walters, T.R. et al, A pilot study of the efficacy and safety of AGN 190342-LF 0.02% and 0.08% in patients with elevated intraocular pressure, ARVO 1991 Annual Meeting Abstract Issue, Invest. Ophthalmol. Vis. Sci., 1991, 988, 32.
Walters, Tom, Development and Use of Brimonidine in Treating Acute and Chronic Elevations of Intraocular Pressure: A Review of Safety, Efficacy, Dose Response, and Dosing Studies, Surv. Ophth., Nov. 1996, S27, 41 (Suppl. 1)
Wang, Rong-Fang et al, Comparison of the Ocular Hypotensive Effect of Brimonidine, Dorzolamide, Latanoprost, or Artificial Tears Added to Timolol in Glaucomatous Monkey Eyes, Journal of Glaucoma, 2000, 458-462, 9, Lippincott Williams & Wilkins, US.
Watson Laboratories, Inc.; "Letter Regarding Combigan® and Notice of Paragraph IV Certification to U.S. Patent Nos.7,030,149; 7,320,976; 7,323,463; and 7,642,258 and Offer of Confidential Access to Watson's ANDA No. 201949"; Jul. 26, 2010.
Wong, Paul, Apoptosis, retinitis pigmentosa, and degeneration, Biochem Cell Biol., Dec. 1994, 489-498, 72(11-12).
Young, Richard, Pathophysiology of Age-related Macular Degeneration, Surv. Ophthalmol., 1987, 291-306, 31(5).
Yuksel, Nursen et al, The Short-Term Effect of Adding Brimonidine 0.2% to Timolol Treatment in Patients with Open-Angle Glaucoma, Ophtalmologica, 1999, 223-233, 213(3).
Craven, Randy et al, Brimonidine and Timolol Fixed-Combination Therapy Versus Monotherapy: A—Month Randomized Trial in Patients with Glaucoma or Ocular Hypertension, Journal of Ocular Pharmacology and Therapeutics, 2005, 337-348, 21(4).
Sherwood, Mark et al, Twice-Daily 0.2% Brimonidine-0.5% Timolol Fixed-Combination Therapy vs Monotherapy With Timolol or Brimonidine in Patients With Glaucoma or Ocular Hypertension, Arch Ophthalmol, 2006, 1230-1238, 124.
Alphagan (Brimonidine Tartrate Ophthalmic Solution) 0.5%, Information Leaflet by Allergan, 2001, 17 Pages.
Burger, Artur et al, Hunnius Pharmazeutisches Worterbuch, 1998, 1000-1001, 102-103.
Burke, James et al, Preclinical Evaluation of Brimonidine, Survey of Ophthalmology, Nov. 1996, S9-S18, 41 (1).
Cantor, Louis, The Evolving Pharmacotherapeutic Profile of Brimonidine, an α2-adrenergic Agonist, After Four Years of Continuous Use, Expert Opinion on Pharmacotherapy, 2000, 815-834, 1(4).
Clinical Study Report: A Multicenter, Double-Masked, Randomized, Parallel Study of the Safety and Efficacy of 0.2% Brimonidine Tartrate/0.5% Timolol Combination Ophthalmic Solution Twice-Daily Compared with 0.5% Timolol Twice-Daily or ALPHAGAN Three-Times-Daily for Three Months (Plus 9-Month, Masked Extension) in Patients with Glaucoma or Ocular Hypertension, 2008, 11 Pages.
Connor, Jennie et al, Driver Sleepiness and Risk of Serious Injury to Car Occupants: Population Based Case Control Study, BMJ, May 11, 2002, 5 Pages, 324.
Correspondence from Feldmann Patentanwaltskanzlei Patent Law Firm "Einwendung Dritter gemab Art. 115 EPU", Oct. 2013, 28 Pages.
Data Sheet for Brimonidine, 2007, 1 Page.
Data Sheet for Timolol, 2007, 1 Page.
EPO Correspondence, Decision of the Technical Board of Appeal Mar. 3, 2002 of Apr. 17, 2012, Apr. 25, 2012, 12 Pages.
Fechtner, Robert et al, The Future of Glaucoma Diagnosis and Therapy, The Future of Glaucoma Diagnosis and Therapy, 2000, 419-426.
Final Study Report, A Comparison of the Safety and Efficacy of Twice-Daily vs. Three-Times-Daily Administration of Brimonidine 0.2%, in Subjects with Open-Angle Glaucoma or Ocular Hypertension, Allergan Study Number: A342-119-7831, 1995, 187 Pages.
Herrin, Stan, What's New in Ophthalmic Drugs, Review of Ophthalmology, Jan. 1998, 77-81.

(56) References Cited

OTHER PUBLICATIONS

Jarvinen, Kristiina et al, Ocular Absorption Following Topical Delivery, Advanced Drug Delivery Reviews, 1995, 3-19, 16.
Lee, David et al, The Effectiveness and Safety of Brimonidine as Mono-, Combination, or Replacement Therapy for Patients with Primary Open-Angle Glaucoma or Ocular Hypertension: A Post Hoc Analysis of an Open-Label Community Trial, Journal of Ocular Pharmacology and Therapeutics, 2000, 3-18, 16(1).
Morrison, John et al, Adjunctive Glaucoma Therapy: A Comparison of Apraclonidine to Dipivefrin When Added to Timolol Maleate, Ophthalmology, 1989, 3-7, 96.
Noecker, Robert, Effects of Common Ophthalmic Preservatives on Ocular Health, Advances in Therapy, Sep.-Oct. 2001, 205-215, 18(5).
Notice of Opposition as filed at the European Patent Office by Abdi Ibrahim Ilac Sanayi ve Ticaret A.S., dated Oct. 10, 2013, 17 Pages.
Notice of Opposition as filed at the European Patent Office by Feldmann in the name of Alfred Tiefenbacher, dated Oct. 8, 2013, 67 Pages.
Notice of Opposition as filed at the European Patent Office by Generics Limited, 2013, 6 Pages.
Notice of Opposition as filed at the European Patent Office by Lederer & Keller on Behalf of Teva Pharmaceutical Industries Ltd., dated Oct. 7, 2013, 11 Pages.
Notice of Opposition as filed at the European Patent Office by Maiwald Patentanwalts GmbH on behalf of STADA Arzneimittel AG, dated Oct. 4, 2013, 16 Pages.
Notice of Opposition as filed at the European Patent Office by Ter Meer Steinmeister & Partner Patentanwalte on behalf of Hexal AG, dated Oct. 9, 2013, 18 Pages.
Ormrod, Douglas et al, Topical Dorzolamide 2%/Timolol 0.5%, Drugs and Aging, Dec. 2000, 477-496, 17(6).
Rote Liste 2001: Arzneimittelverzeichnis Fur Deutschland, 2001, 16 Pages.
Stamper, Robert, Primary Drug Treatment for Glaucoma: Beta-Blockers Versus Other Medications, Survey of Ophthalmology, Jan.-Feb. 2002, 63-67, 47(1).
Stewart, William, Chronic Open-Angle Glaucoma and Lifestyle, Progress in Retinal and Eye Research, 1997, 567-590, 16(4).
Submission to European Patent Office for European Patent Application No. 03726234.2, dated Mar. 14, 2012, 8 Pages.
Submission to European Patent Office for European Patent Application No. 03726234.2-2123, dated Aug. 19, 2011, 6 Pages.
Summons to Oral Proceedings Pursuant to Rule 115(1) EPC in Case T 1064/08 + Annex, Nov. 14, 2011, 11 Pages.
U.S. Appl. No. 10/126,790, filed on Apr. 19, 2002.
Wigginton, Stephen et al, Choosing Beta-Blockers for Initial Medical Therapy for Glaucoma, Surv Ophthalmol, Jan. 2002, 68-73, 47(1).
Wigginton, Stephen et al, Choosing Initial and Combination Medical Therapy for Glaucoma, Glaucoma Diagnosis and Management, Sep. 2000, 417-427, vol. 13, No. 3.
Motolko, Michael A., Comparison of allergy rates in glaucoma patients receiving brimonidine 0.2% monotherapy versus fixed-combination brimonidine 0.2%-timolol 0.5% therapy*, Current Medical Research and Opinions, vol. 24, No. 9, 2008, pp. 2663-2667.

COMBINATION OF BRIMONIDINE AND TIMOLOL FOR TOPICAL OPHTHALMIC USE

CROSS-REFERENCE TO RELATED APPLICATIONS

The present application is continuation of U.S. patent application Ser. No. 13/801,252, filed Mar. 13, 2013, which is a continuation of U.S. patent application Ser. No. 13/727,106, filed Dec. 26, 2012, which is a continuation of U.S. patent application Ser. No. 13/308,507, filed Nov. 30, 2011, now U.S. Pat. No. 8,354,409, issued Jan. 15, 2013, which is a continuation of U.S. patent application Ser. No. 11/946,828, filed Nov. 28, 2007, now U.S. Pat. No. 8,133,890, issued Mar. 13, 2012, which is a continuation of U.S. patent application Ser. No. 10/685,941, filed Oct. 14, 2003, now U.S. Pat. No. 7,320,976, issued Jan. 22, 2008, which is a continuation of U.S. patent application Ser. No. 10/126,790, filed on Apr. 19, 2002, now U.S. Pat. No. 7,030,149, issued Apr. 18, 2006, the disclosures of which are hereby incorporated in their entirety herein by reference.

BACKGROUND

This invention relates to the topical ophthalmic use of brimonidine in combination with timolol when indicated for treatment of glaucoma or ocular hypertension. Such combinations or formulations are available for separate use in the ophthalmic art and have been combined in serial application during the course of treatment of glaucoma. However, there are concerns and expressed reservations in the ophthalmic community about patient compliance when the patient is required to administer separate medications to treat a single disease or condition such as glaucoma. There is, moreover, a long felt need for an effective and safe topical ophthalmic pharmaceutical composition including brimonidine and timolol which has increased stability and requires a lower effective concentration of preservative as compared to the individual agents taken alone. Finally, there is a need to increase the efficacy of many topical ophthalmic agents, without increasing the systemic concentration of such topical agents, since it is well known that many of such topically-applied ophthalmic agents cause systemic side effects, e.g. drowsiness, heart effects, etc. Unexpectedly it has been discovered that brimonidine in combination with timolol meets these criteria.

Brimonidine is disclosed in U.S. Pat. No. 3,890,319. The use of brimonidine for providing neuroprotection to the eye is disclosed in U.S. Pat. Nos. 5,856,329; 6,194,415 and 6,248,741.

Timolol, as an ophthalmic drug, is disclosed in U.S. Pat. Nos. 4,195,085 and 4,861,760.

DESCRIPTION OF THE INVENTION

Brimonidine is an alpha adrenergic agonist represented by the following formula:

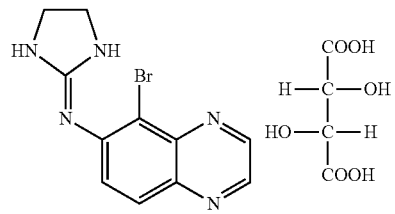

The chemical name for brimonidine is 5-Bromo-6-(2-imidazolidinylideneamino)quinoxaline L-tartrate.

Timolol is a beta adrenergic agent represented by the following formula:

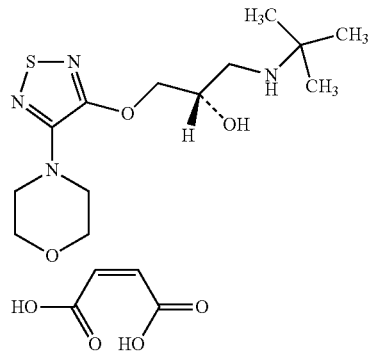

Brimonidine is available from Allergan, Inc., Irvine, Calif. as an ophthalmic pharmaceutical product having the name Alphagan®.

Timolol is available from various sources, including Merck Co., Rahway, N.J.

The compositions of the present invention are administered topically. The dosage is 0.001 to 1.0, e.g. mg/per eye BID; wherein the cited mass figures represent the sum of the two components, brimonidine and timolol. The compositions of the present invention can be administered as solutions in a suitable ophthalmic vehicle.

In forming compositions for topical administration, the mixtures are preferably formulated as 0.01 to 0.5 percent by weight brimonidine and 0.1 to 1.0 percent by weight timolol solution in water at a pH of 4.5 to 8.0, e.g. about 6.9. While the precise regimen is left to the discretion of the clinician, it is recommended that the solution be topically applied by placing one drop in each eye two times a day. Other ingredients which may be desirable to use in the ophthalmic preparations of the present invention include preservatives, co-solvents and viscosity building agents.

Antimicrobial Preservative:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, typically such preservatives are employed at a level of from 0.004% to 0.02%. In the compositions of the present application the preservative, preferably benzalkonium chloride, may be employed at a level of from 0.001% to less than 0.01%, e.g. from 0.001% to 0.008%, preferably about 0.005% by weight. It has been found that a concentration of benzalkonium chloride of 0.005% is sufficient to preserve the compositions of the present invention from microbial attack. This concentration may be advantageously compared to the requirement of 0.01% benzalkonium chloride to preserve timolol in the individual, commercially-available ophthalmic products. Moreover, it has been found that adequate lowering of intraocular pressure has been obtained when administering the compositions of this invention twice a day as compared to the FDA-approved regimen wherein brimonidine ophthalmic solution, i.e. Alphagan® ophthalmic solution is administered three times a day and timolol ophthalmic solution, i.e. Timoptic® ophthalmic solution is administered twice a day. This results in the exposure of the patient to 67% and 50% of benzalkonium chloride, with the compositions of this invention, as compared to the administration of Alphagan® and Timoptic®, respectively. In FDA-approved adjunctive therapy, wherein Alphagan® and Timoptic® are serially administered, the patient is exposed to almost three times the concentration of benzalkonium chloride as compared to the administration of the compositions of this invention twice a day. (It is noted that it is known that benzalkonium chloride at high concentrations is cytotoxic. Therefore, minimizing the patient's exposure to benzalkonium chloride, while providing the preservative effects afforded by benzalkonium chloride, is clearly desirable.)

Co-Solvents:

The solubility of the components of the present compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Typically such co-solvents are employed at a level of from 0.01% to 2% by weight.

Viscosity Agents:

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity building agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The present invention further comprises an article of manufacture comprising packaging material and a pharmaceutical agent contained within said packaging material, wherein the pharmaceutical agent is therapeutically effective for lowering intraocular pressure and wherein the packaging material comprises a label which indicates the pharmaceutical agent can be used for lowering intraocular pressure and wherein said pharmaceutical agent comprises an effective amount of brimonidine and an effective amount of timolol.

The following example is a representative pharmaceutical composition of the invention for topical use when indicated for treating glaucoma.

EXAMPLE I

The combination of active pharmaceutical ingredients is as follows:
Brimonidine Tartrate 0.20% (w/v) and Timolol Maleate 0.68% (w/v)
(Equivalent to 0.50% (w/v) timolol)
The Brimonidine-Timolol combination formulation presented in the Table, below, is a sterile, preserved, aqueous solution. The formulation vehicle is based upon a timolol ophthalmic solution which contains an isotonic phosphate buffer system at pH 6.9. The formulation preservative is benzalalkonium chloride (BAK) at a concentration of 0.005% (w/v) (50 ppm). The formulation passes regulatory required preservative efficacy testing (PET) criteria for USP (United States Pharmacopoeia) and EP (European Pharmacopoeia-A and -B over 24 months.

TABLE

| Ingredient | Function | Concentration, %(w/v) |
|---|---|---|
| Brimonidine Tartrate | Active | 0.2 |
| Timolol Maleate, EP | Active | 0.68[1] |
| Benzalkonium Chloride, NF, EP | Preservative | 0.005 |
| Sodium Phosphate, monobasic monohydrate, USP | Buffer | 0.43 |
| Sodium Phosphate, dibasic heptahydrate, USP | Buffer | 2.15 |
| Sodium Hydroxide, NF | pH adjust | Adjust pH to 6.9 |
| Hydrochloric Acid, NF | pH adjust | Adjust pH to 6.9 |
| Purified Water, USP, EP | Solvent | q.s. ad |

[1]Equivalent to 0.5%(w/v) Timolol, free base

The pharmaceutical composition of Example I is used in the clinical study reported below.

EXAMPLE II

Objectives:

To compare the safety and efficacy of twice-daily dosed brimonidine tartrate 0.2%/timolol 0.5% ophthalmic solution combination (henceforth referred to as Combination) with that of twice-daily dosed timolol ophthalmic solution 0.5% (henceforth referred to as Timolol) and three-times-daily dosed ALPHAGAN® (brimonidine tartrate ophthalmic solution) 0.2% (henceforth referred to as Brimonidine) administered for three months (plus 9-month masked extension) in patients with glaucoma or ocular hypertension.

Methodology:

Structure: multicenter, double-masked, randomized, parallel-group, active control;

Randomization: patients were randomized to one of the 3 masked treatment groups (Combination, Brimonidine or Timolol) based on an even allocation at each site;

Visit Schedule: prestudy, baseline (day 0), week 2, week 6, month 3, month 6, month 9, and month 12.

Number of Patients (Planned and Analyzed):

560 planned to enroll; 586 enrolled (Combination=193, Brimonidine=196, Timolol=197); 502 completed. Mean (range) age: 62.4 (23 to 87) years; 46.1% (270/586) males, 53.9% (316/586) females.

Diagnosis and Main Criteria for Inclusion:

Diagnosis: ocular hypertension, chronic open-angle glaucoma, chronic angle-closure glaucoma with patent iridotomy, pseudoexfoliative glaucoma or pigmentary glaucoma and requiring bilateral treatment;

Key Inclusion Criteria: ≥18 years, day 0 (post-washout) intraocular pressure (IOP)≥22 mm Hg and ≤34 mm Hg in each eye and asymmetry of IOP≤5 mm Hg, best-corrected Early Treatment of Diabetic Retinopathy Study (ETDRS) visual acuity equivalent to a Snellen score of 20/100 or better in each eye;

Key Exclusion Criteria: uncontrolled systemic disease, abnormally low or high blood pressure or pulse rate for age or contraindication to beta-adrenoceptor antagonist therapy, anticipated alteration of existing chronic therapy with agents which could have a substantial effect on IOP, contraindication to brimonidine therapy, allergy or sensitivity to any of the study medication ingredients, anticipated wearing of contact lenses during the study, laser surgery, intraocular filtering surgery or any other ocular surgery within the past 3 months, or required chronic use of other ocular medications during the study (intermittent use of artificial tear product was allowed).

Test Product, Dose and Mode of Administration, Batch Number:

Brimonidine tartrate 0.2%/timolol 0.5% combination ophthalmic solution one drop (~35 µL) instilled in each eye BID in the morning and evening; and vehicle of the Combination ophthalmic solution, one drop (~35 µL) instilled in each eye once daily (QD) in the afternoon (for masking purposes).

Duration of Treatment: 3 months (with a 9-month masked extension).

Reference Therapy, Dose and Mode of Administration, Batch Number:

Active control ALPHAGAN® (brimonidine tartrate ophthalmic solution) 0.2%, one drop (~35 µL) instilled in each eye TID in the morning, afternoon, and evening.

Active control timolol ophthalmic solution 0.5%, one drop (~35 µL) instilled in each eye BID in the morning and evening; and vehicle of the Combination ophthalmic solution, one drop (~35 µL) instilled in each eye once daily (QD) in the afternoon (for masking purposes).

Criteria for Evaluation:

Efficacy: IOP (hours 0, 2, 7, and 9), patient satisfaction questionnaire, patient comfort of study medication questionnaire, pharmacoeconomic evaluation by investigator;

Safety: Adverse events (AE), biomicroscopy, visual acuity (VA), visual field, ophthalmoscopy, cup/disc ratio, heart rate, blood pressure, hematology, serum chemistry, urinalysis and pregnancy test;

Other: Quantitation of plasma brimonidine and timolol concentrations (at selected sites), resource utilization (to be reported upon completion of the 1 year study).

Statistical Methods:

All data were summarized with descriptive statistics, frequency tables, and/or data listings. Safety analyses included all patients who received at least 1 dose of study medication. Analyses were performed for the primary efficacy variable IOP using the intent-to-treat (ITT) population with last observation carried forward (LOCF), and the per protocol population with observed cases.

Ordinal categorical variables were analyzed by the Wilcoxon rank-sum test. Nominal categorical variables were analyzed using Fisher's exact or Pearson's chi-square tests. Within-group changes from baseline for categorical variables were analyzed using the Wilcoxon signed-rank test. Continuous variables (eg, IOP) were analyzed using analysis of variance (ANOVA). Within-group changes from baseline for continuous variables were analyzed using paired t-tests.

A 2-way ANOVA model with factors for treatment and investigator was used for the analysis of IOP. Comparisons were made between the Combination and each of the 2 monotherapies in a pairwise fashion using contrasts from the ANOVA model, with the same error term. A separate ANOVA model was employed at each hour/visit measurement of IOP. Each of the 2 null hypotheses (Combination versus Timolol and Combination versus Brimonidine) was tested at the 0.05 significance level. Point estimates of the mean treatment differences, as well as 2-sided 95% confidence intervals (CI) of the difference, were provided at each timepoint.

Summary—Conclusions:

Efficacy: At baseline, mean values of diurnal IOP ranged from 22.2 mm Hg to 24.9 mm Hg in the Combination group, 22.5 mm Hg to 25.0 mm Hg in the Brimonidine group, and 22.3 mm Hg to 24.8 mm Hg in the Timolol group. There were no statistically significant differences between treatment groups.

Mean changes from baseline diurnal IOP at week 2, week 6 and month 3 ranged from:
 −5.2 to −7.9 mm Hg in the Combination group
 −3.5 to −5.7 mm Hg in the Brimonidine group
 −4.5 to −6.4 mm Hg in the Timolol group The mean decreases from baseline diurnal IOP were statistically significant within each treatment group at each follow-up timepoint ($p<0.001$).

The mean decrease from baseline diurnal IOP was statistically significantly greater with Combination than with Brimonidine at hours 0, 2, and 7 at all follow-up visits ($p<0.001$). In addition, clinically significant differences of more than 1.5 mm Hg in mean change from baseline IOP favoring Combination over Brimonidine were seen at hours 0, 2, and 7 at all follow-up visits. At hour 9, the decreases from baseline diurnal IOP were greater for the Combination group than the Brimonidine group at all follow-up visits, although the differences were not statistically significant ($p \geq 0.104$). The mean decrease from baseline diurnal IOP was statistically significantly greater with Combination than with Timolol at hours 0, 2, 7 and 9 at all follow-up visits ($p \leq 0.041$). In addition, clinically significant differences of more than 1.5 mm Hg in mean change from baseline IOP favoring Combination over Timolol were seen at week 2 (hours 0, 2, and 7), week 6 (hours 2 and 7), and month 3 (hours 0 and 2).

Mean values of diurnal IOP at week 2, week 6 and month 3 ranged from:
 15.9 to 18.1 mm Hg in the Combination group
 17.4 to 21.5 mm Hg in the Brimonidine group
 17.5 to 18.9 mm Hg in the Timolol group Mean values of diurnal IOP were statistically significantly less with Combination than with Brimonidine at hours 0, 2, and 7 at all follow-up visits ($p<0.001$) and at hour 9 at week 6 and month 3 ($p \leq 0.011$). The mean values of IOP at hour 9 at week 2 were lower for the Combination group than the Brimonidine group, although the difference was not statistically significant ($p=0.205$). In addition, clinically significant differences of more than 1.5 mm Hg in mean IOP favoring Combination over Brimonidine were seen at hours 0, 2, and 7 at all follow-up visits and at hour 9 at month 3.

Mean values of diurnal IOP were statistically significantly less with Combination than with Timolol at hour 0 at week 2 and month 3; and at hours 2, 7 and 9 at all follow-up visits ($p \leq 0.050$). The mean values of IOP at hour 0, week 6, were lower for the Combination group than the Timolol group, although the difference was not statistically significant ($p=0.102$). In addition, clinically significant differences of more than 1.5 mm Hg in mean IOP favoring Combination over Timolol were seen at week 2 (hours 0, 2, and 7), week 6 (hours 2, 7, and 9), and month 3 (hours 2 and 9).

At the month 3 or exit visit, a statistically significantly greater "yes" response to the Investigator Pharmacoeconomic Evaluation was recorded for patients receiving Combination (91.1%, 173/190) than for patients receiving Brimonidine (73.4%, 141/192, $p<0.001$). A "yes" response was recorded for 92.7% (179/193) of patients receiving Timolol. There were no statistically significant differences in the change from baseline in treatment comfort between Combination and each of the monotherapy groups.

Treatment satisfaction was better than baseline for a statistically significantly greater percentage of patients in the Combination group (23.4%, 36/154) than in the Brimonidine group (13.2%, 20/151, p=0.005). A total of 19.9% (30/151) of patients in the Timolol group reported better treatment satisfaction than baseline.

Safety:

Through month 3 of the study, 53.4% (103/193) of patients in the Combination group, 61.7% (121/196) of the Brimonidine group, and 50.8% (100/197) of the Timolol group experienced one or more adverse events, regardless of causality. The incidences of oral dryness, eye pruritus, foreign body sensation and conjunctival folliculosis were statistically significantly lower with the Combination than with Brimonidine ($p \leq 0.034$), while burning and stinging were statistically significantly higher with the Combination than with Brimonidine ($p \leq 0.028$). There were no statistically significant differences in adverse events between the Combination and Timolol, except for a statistically significantly higher incidence of eye discharge with the Combination (2.6%, 5/193) compared to Timolol (0%, 0/197; p=0.029). The most frequently reported adverse events (>3% in any treatment group) were as follows, tabulated by descending order in the Combination group:

| Preferred Term | Combination N = 193 | Brimonidine N = 196 | Timolol N = 197 |
| --- | --- | --- | --- |
| burning sensation in eye | 23 (11.9%) | 11 (5.6%) | 25 (12.7%) |
| conjunctival hyperemia | 16 (8.3%) | 23 (11.7%) | 11 (5.6%) |
| stinging sensation eye | 13 (6.7%) | 4 (2.0%) | 11 (5.6%) |
| infection (body as a whole) | 11 (5.7%) | 6 (3.1%) | 8 (4.1%) |
| visual disturbance | 6 (3.1%) | 11 (5.6%) | 3 (1.5%) |
| epiphora | 5 (2.6%) | 8 (4.1%) | 3 (1.5%) |
| oral dryness | 4 (2.1%) | 19 (9.7%) | 1 (0.5%) |
| eye pruritus | 3 (1.6%) | 13 (6.6%) | 3 (1.5%) |
| allergic conjunctivitis | 3 (1.6%) | 7 (3.6%) | 0 (0.0%) |
| asthenia | 3 (1.6%) | 6 (3.1%) | 1 (0.5%) |
| foreign body sensation | 2 (1.0%) | 10 (5.1%) | 5 (2.5%) |
| conjunctival folliculosis | 2 (1.0%) | 9 (4.6%) | 1 (0.5%) |
| somnolence | 2 (1.0%) | 7 (3.6%) | 0 (0.0%) |

Adverse events led to the discontinuation of 3.6% (7/193) of patients in the Combination group, similar to 3.0% (6/197) of patients in the Timolol group, and statistically significantly less than 14.3% (28/196) of patients in the Brimonidine group (p<0.001). Serious adverse events were reported for 1.0% (2/193) of patients in the Combination group, 2.0% (4/196) of patients in the Brimonidine group, and 2.0% (4/197) of patients in the Timolol group. Two patients receiving Timolol had 4 serious adverse events (emphysema in one patient; nausea, sweating, and tachycardia in the other patient) which were considered possibly related to the study drug. There was 1 death in the Brimonidine group, possibly due to complications from cardiac surgery, and not related to study drug.

There were no clinically relevant differences between the Combination and either of the individual components in the mean change from baseline to month 3 for any hematology, chemistry, or urinalysis parameter. Statistically significant ($p \leq 0.048$) within-group changes from baseline were found, but were small and not clinically relevant.

Small but statistically significant ($p \leq 0.001$) mean reductions in heart rate ranging from −2.1 to −3.7 bpm were seen with the Combination, similar to Timolol. Small but statistically significant ($p \leq 0.003$) mean reductions in blood pressure at hour 2 (postdose) were seen with the Combination, similar to Brimonidine. These small changes in mean heart rate and blood pressure were associated with clinical symptoms in only a few patients.

Increases from baseline in the severity of conjunctival erythema and conjunctival follicles on biomicroscopy were statistically significantly less with the Combination than with Brimonidine ($p \leq 0.011$). The majority of patients in each treatment group showed less than a 2-line change from baseline visual acuity. There were no significant between-group differences for changes in visual fields or cup/disc ratio.

Pharmacokinetics:

Blood samples were available for 55 patients in the Combination group, 49 patients in the Brimonidine group, and 54 patients in the Timolol group. All samples were assayed for both brimonidine (lower limit of quantitation [LLOQ] 5 pg/mL) and timolol (LLOQ 5 pg/mL). Plasma brimonidine and timolol concentrations were not quantifiable in all but 1 sample on day 0, hour 0 for both Combination and the monotherapy treatment groups.

In the Combination group, mean±standard deviation (SD) plasma brimonidine concentrations 1 hour postdose at week 2 and month 3 were 49.7±36.1 and 52.8±46.7 pg/mL, respectively. In the Brimonidine group, mean±SD plasma brimonidine concentrations at week 2 and month 3 were 81.0±63.8 and 78.6±48.9 pg/mL, respectively. In the Combination group, mean±SD plasma timolol concentrations at week 2 and month 3 were 0.499±0.327 and 0.586±0.580 ng/mL, respectively. In the Timolol group, mean±SD plasma timolol concentrations at week 2 and month 3 were 0.950±0.709 and 0.873±0.516 ng/mL, respectively.

Plasma brimonidine and timolol concentrations 1 hour postdose were steady and did not increase over the 3-month study duration. Brimonidine concentrations were 39%, 34% and 39% lower in the Combination group than in the monotherapy group at week 2 (p=0.004), month 3 (p=0.013), and month 12, respectively. Timolol concentrations were 47% and 33% lower in the Combination group than in the monotherapy group at week 2 (p<0.001) and month 3 (p=0.011), respectively.

Timolol concentrations were also significantly lower in the combination treatment group than in the Timolol monotherapy treatment group (p=0.0006). Timolol concentrations were 49%, 32%, and 21% lower in the combination group than in the monotherapy group at week 2, month 3, and month 12, respectively.

The plasma brimonidine concentration in males was statistically significantly lower than in females for the Brimonidine group (37% lower at week 2 [p=0.034] and 37% lower at month 3 [p=0.017]); the difference was not statistically significant in the Combination group. The plasma timolol concentration in males was statistically significantly lower than in females for both the Combination group (not statistically significant at week 2; 52% lower at month 3 [p=0.012]) and the Timolol group (45% lower at week 2 [p=0.006] and 39% lower at month 3 [p=0.003]).

Plasma brimonidine concentration in the elderly group was not significantly different from in the young group for the combined data from both the combination and Brimonidine treatment groups (p-value=0.1323). However, plasma timolol concentration in the young group was significantly lower than in the elderly group for combined data from both the combination and the Timolol treatment groups (p-value=0.0005).

CONCLUSIONS

The Combination treatment (brimonidine tartrate 0.2%/timolol 0.5%) administered BID for 3 months was superior to Timolol (timolol 0.5%) BID and Brimonidine (brimonidine tartrate 0.2%) TID in lowering the elevated IOP of patients with glaucoma or ocular hypertension. The Combination administered BID demonstrated a favorable safety profile that was comparable to Timolol BID and better than Brimonidine TID with regard to the incidence of adverse events and discontinuations due to adverse events.

The invention has been described herein by reference to certain preferred embodiments. However, as obvious variations thereon will become apparent to those skilled in the art, the invention is not to be considered as limited thereto.

What is claimed is:

1. A method of treating a patient with glaucoma or ocular hypertension comprising administering twice daily to an affected eye a single composition comprising 0.2% w/v brimonidine tartrate and 0.5% w/v timolol free base, wherein said method reduces the incidence of one or more adverse events, as compared to the administration of 0.2% w/v brimonidine tartrate monotherapy three times per day wherein the adverse event is selected from the group consisting of conjunctival hyperemia, oral dryness, eye pruritus, allergic conjunctivitis, foreign body sensation, conjunctival folliculosis, and somnolence.

2. The method of claim 1, wherein the adverse event is conjunctival hyperemia.

3. The method of claim 1, wherein the adverse event is oral dryness.

4. The method of claim 1, wherein the adverse event is eye pruritus.

5. The method of claim 1, wherein the adverse event is allergic conjunctivitis.

6. The method of claim 1, wherein the adverse event is foreign body sensation.

7. The method of claim 1, wherein the adverse event is conjunctival folliculosis.

8. The method of claim 1, wherein the adverse event is somnolence.

* * * * *